United States Patent [19]

Pugia

[11] Patent Number: 5,096,827
[45] Date of Patent: Mar. 17, 1992

[54] COMPOSITION FOR PREVENTING UNWANTED OXIDATION OF REDOX INDICATORS

[75] Inventor: Michael J. Pugia, Granger, Ind.

[73] Assignee: Miles Inc., Elkhart, Ind.

[21] Appl. No.: 284,685

[22] Filed: Dec. 15, 1988

[51] Int. Cl.$^5$ ............................................. C01N 31/00
[52] U.S. Cl. ........................................ 436/8; 436/18
[58] Field of Search .................... 252/42.7, 46.3, 51.5, 252/186.1, 186.2, 186.25, 186.27, 186.38, 186.43, 186.28, 191, 192; 436/514, 501, 135, 174, 175, 8, 18; 435/805, 8, 10, 28

[56] References Cited

U.S. PATENT DOCUMENTS 3,411,887 11/1969 Ku ............................................. 435/8

OTHER PUBLICATIONS

"Kinetics and Mechanism of the Oxidation of L-Ascorbic Acid by Tris-(Oxalato) Cobaltate (III) and Tris (1,10-Phenanthroline) Iron (III) Complexes in Aqueous Solution", Kimura et al., J. C. S. Dalton; 423-427.
"Cobalt-Induced Activation of Hydrogen Peroxide for the Direct Ketonization of Methylenic Carbons [c-$C_6H_{12}$→c-$C_6H_{10}$(O)], The Oxidation of Alcohols and Aldehydes, and the Dioxygenation of Aryl Olefins and Acetylene", Sawyer et al., J. Am. Chem. Soc. 112; 8214-8214; 1990.
"Cobalt (III) Alkylperoxy Complexes Synthesis, X-ray Structure, and Role in the Catalytic Decomposition of Alkyl Hydroperoxides and in the Hydroxylation of Hydrocarbons", Mimoun et al., J. Am. Chem. Soc. 107(12); 3534-3540.
"Removal of Ascorbate Inhibition in the Glucose and Occult Blood Urine Test Strips Status Report", John E. Sheats, Professor of Chemistry, Rider College, Lawrence, N.J.; 5-9; 01 Aug. 1979.
Peinado et al., *Analytica Chimica Acta*, 184 (1986), 235-42.
Pantel, S., *Analytica Chimica Acta*, 104, (1979), 205-13.
*The Merk Index*, 8th Edition, Merk and Co., Inc., Rahway, N.J., 1968, pp. 1127, 273, 642.

*Primary Examiner*—David L. Lacey
*Assistant Examiner*—Thomas E. Daley
*Attorney, Agent, or Firm*—Roger N. Coe

[57] ABSTRACT

The present invention is directed to a reliable redox indicator composition for use in chemical assay systems and is particularly well suited for assay systems using a dry phase format. More specifically, the improved indicator composition of this invention is directed to the use of a divalent metal complex to prevent unwanted metal hydroperoxide mediated and similar-type oxidation of redox indicators. A fundamental element of the present invention involves the use of divalent metal complexes of the general formula:

$$(CH_3-\overset{\overset{\displaystyle O}{\|}}{C}-O)_2M$$

wherein M is either Zn(II), Co(II), Mn(II), or Rb(II).

5 Claims, No Drawings

COMPOSITION FOR PREVENTING UNWANTED OXIDATION OF REDOX INDICATORS

BACKGROUND OF THE INVENTION

1. Field of the Invention

The present invention is directed to a reliable redox indicator system for use in chemical assay systems. The invention is particularly well suited for assay systems using a dry phase format. More specifically, the improved indicator system of this invention is directed to the use of a divalent metal complex to prevent metal hydroperoxide mediated or similar-type oxidation of redox indicators.

2. Discussion of the Prior Art

Ascorbic acid is an important and well known nutrient which exists naturally in many foods, such as fruits and vegetables, and can also be synthesized inexpensively as a food additive or vitamin supplement. As a result, ascorbic acid is relatively plentiful, and the general population tends to ingest more ascorbic acid than necessary.

Excess ascorbic acid is generally not harmful, because the body will only absorb ascorbic acid in an amount sufficient to meet the body's short term needs, quickly disposing of the excess by means of the body's urinary system. As a result, ascorbic acid is often found in urine samples used in medical analysis.

Unfortunately, ascorbic acid in urine can be an unwanted interferant for many urine assays presently in existence. Urine assays in general are an important medical tool in diagnosing and treating the general population, and therefore much attention has been focused upon this problem in recent years.

Urine assays often comprise redox indicators, and these indicators are generally incorporated into the assay system in their reduced form. The indicators will change color when oxidized and are therefore called "redox" indicators, because they change colors as they move from a reduced to an oxidized state due to the presence of an oxidizer.

In many assay systems, an analyte of interest will directly or indirectly cause the oxidation of the assay's redox indicator, thereby causing a detectable response which correlates with the presence of the analyte. In other words, when the appropriate analyte is added to the assay system, the redox indicators will undergo the following reaction:

$$I_{red} \rightarrow I_{ox} + _{at\ least}\ 1\ electron$$

wherein $I_{red}$ is the indicator in a reduced state (negative color response) and where $I_{ox}$ is the indicator in an oxidized stated (positive color response).

However, ascorbic acid in solution undergoes the following reaction:

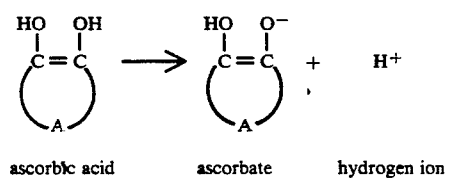

where A is defined as $C_4H_bO_4$. Ascorbate is a reductant, because it is able to donate an electron and thereby reduce the substance receiving the electron:

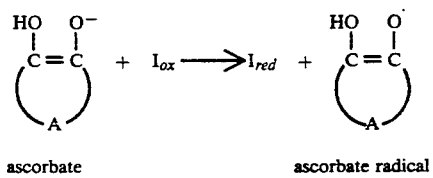

In this way, ascorbate can interfere with a redox indicator by reducing the indicator when it is in its oxidized form, thereby inhibiting the intended color change and causing a "false negative."

Numerous methods have been tried, some successfully, which eliminate the adverse affect ascorbic acid can have upon redox indicators in an assay system. One successful method is disclosed in U.S. Pat. No. 4,587,220 by Mayambala-Mwanika, et al., whereby ferric complexes are combined with hydroperoxide to act as an ascorbate scavenger. This scavenger system prevents ascorbate reduction of redox indicators.

In Mayambala, $Fe^{+3}$ is complexed with an iron chelate such as HEDTA (N-2-hydroxyethylethylenediaminetriacetic acid) and reacted with ascorbic acid. The Fe(III) chelate scavenges ascorbic acid as follows:

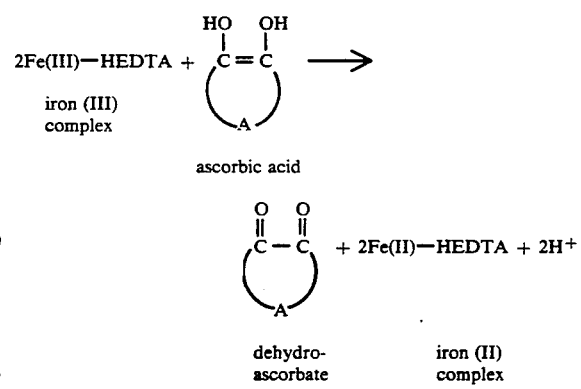

The Mayambala scavenger causes the secondary alcohol groups in ascorbic acid to be oxidized into ketones, and in this way ascorbic acid is transformed into a non-reductant compound which will not interfere with a redox indicator system. However, the Fe(II)-HEDTA is recycled back into Fe(III)-HEDTA using a peroxide or hydroperoxide as follows:

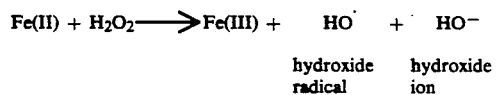

The resulting hydroxide radical can receive an electron according to the following reaction:

can therefore act as an oxidizer. As a result, the hydroxide radical can oxidize the redox indicator when the indicator is in its reduced (original) form, thereby causing a color change regardless of whether or not an analyte of interest is present. Consequently, in preventing a false negative due to ascorbic acid, the ascorbic acid scavenger system of Mayambala can cause an unwanted false positive. In solving one problem, the ascorbic acid scavenger system creates another.

The Mayambala patent suggests an adjustment of the assay's pH by means of conventional buffers to minimize the oxidation affect of the scavenger system. Indeed, since oxidation reactions are typically acid catalyzed and different oxidation reactions can involve different kinetic interactions, it may be possible to find a pH which would accelerate indicator oxidation due to the analyte without substantially accelerating indicator oxidation due to the ascorbic acid scavenger system.

The Mayambala patent also suggests a dry phase format which separates the reagent system into two dip solutions. One dip solution is incorporated and dried on a support and thereafter the second dip solution is also incorporated and dried onto the support. Mayambala therefore suggests that certain constituents of a reagent system can perhaps be separated in a dry format in a manner where the desired oxidation reaction will dominate over the unwanted oxidation reaction.

However, pH adjustment may not prove to be advantageous for every reagent system, and a multidip process for creating a dry phase system may not always be practical or workable for every reagent system. Furthermore, a liquid format may in some cases be more desirable than a dry phase format.

Consequently, it is an object of the present invention to provide a system whereby ascorbate or similar-type reductant interference can be eliminated without adversely affecting the reliability of a redox indicator system.

A further object of the present invention is to provide an ascorbate resistant assay system which can be used in solution form or can be incorporated into a reagent strip using a one dip method.

Other objects and features of the present invention will become apparent to one of ordinary skill in the art upon the reading of the following specification.

SUMMARY OF THE INVENTION

The present invention is directed to a reliable redox indicator composition for use in any one of a number of chemical assay systems and is particularly well suited for assay systems using a dry phase format. More specifically, the improved indicator composition of this invention is directed to the use of a divalent metal complex to prevent unwanted metal hydroperoxide mediated and similar-type oxidation of redox indicators. A fundamental element of the present invention involves the use of divalent metal complexes of the general formula:

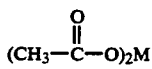

wherein M is either Zn(II), Co(II), Mn(II), or Rb(II).

DETAILED DESCRIPTION OF THE PREFERRED EMBODIMENT

The present invention is directed to the use of divalent metal complexes of the general formula:

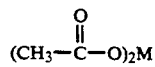

in which M is Zn(II), Co(II), Mn(II), or Rb(II). In a preferred embodiment M is Zn(II).

The preferred concentration of such complexes is about 15 millimolar, although as little as about 5 millimolar will typically provide satisfactory results. Concentrations greater than 15 millimolar can provide satisfactory results, depending, however, upon the reagent system being used.

In use, an ascorbic acid scavenger system, such as the one disclosed in Mayambala, can be used to transform ascorbic acid into a nonreductant substrate. Any resulting oxidant created by the scavenger system can be effectively eliminated using the divalent metal complexes defined above. These complexes will not interfere with conventional redox indicator systems, and can be selectively used to scavenge unwanted hydroxide radical or similar-type oxidizing agents.

In a preferred embodiment of this invention, the above-defined metal complexes are used to prevent ferric-hydroperoxide mediated oxidation of redox indicators (unwanted oxidation due to the ascorbate scavenger system described in Mayambala). The antioxidant behavior of the metal complexes of this invention allows the combination of ferric complexes (such as those described in Mayambala), hydroperoxides, peroxides, and redox indicators without a false negative or false positive reaction in dry phase or solution format and in pH ranges commonly used in urine assay systems.

The metal complexes of this invention have been found to prevent background redox indicator oxidation due to unwanted hydroxide radical and similar type oxidizing agents in either solution or dry phase reagent systems. These metal complexes can be used in conventional acidic or basic pH ranges for either solution or dry reagent assays.

As a result, the assay's reagent system can be buffered to an optimal pH without concern as to ascorbate (or similar-type reductant) interference or interference due to ascorbate scavenger systems which produce hydroxide radical or similar-type oxidation interference. Since the metal complexes of this invention can eliminate hydroxide radical or similar type oxidation interference in solution or dry phase form, there is no need to use a multi-dip dry phase manufacturing process. Furthermore, metal complexes of this invention do not interfere with indicator oxidation by peroxidases, hydroperoxide or other similar-type oxidizing agents commonly used in colorimetric assay systems.

EXAMPLES

Solution Assay

Formula:

One part aqueous buffer at pH=5.8 is combined with two parts of 90% acetonitrile-water containing other chemical components to make a 60% acetonitrile-water solution with the following concentrations.

| Component | Concentration mM (millimolar) |
| --- | --- |
| Buffer: N-(2-Acetamido)iminodiacetic Acid (ADA) | 450 |
| Tetramethylbenzidine (TMB) | 62.5 |

-continued

| Component | Concentration mM (millimolar) |
| --- | --- |
| Diisopropylbenzene dihydroperoxide (DBDH) | 125 |
| Ferric chloride | 9.3 |
| N(2-hydroxyethyl)ethylenediamine triacetic acid | 9.3 |
| Cobalt II, Zinc II or Manganese II, Rubidium II or acetate | 37.2 |

Analysis:

Various hemoglobin levels were added to a UV-VIS (UV-visible) cuvette containing the above solution. The absorbance of the resultant color produced was recorded at 660 nm (nanometers) and rates of color formation were calculated.

Results:

A solution containing all of the listed components except cobalt II, zinc II, manganese II, or rubidium II acetate produced a large 600 nm absorbance which was at the instrumental detection limit and thus prevented any detection of hemoglobin. When cobalt II, zinc II, manganese II or rubidium II acetates were included with the other solution components, the absorbance at 660 nm was very small and hemoglobin concentrations of 0.010 mg/dL (milligrams per deciliter) were easily detected by absorbance changes. Absorbance was directly proportional to hemoglobin concentration. The addition of 109 mM ascorbic acid had no affect on the absorbance produced by the 0.045 mg/dL hemoglobin.

Antioxidant behavior was not observed with manganese valance states such as manganese III acetate or anions such as manganese II nitrate, carbonate, ammonium, chloride or sulfonate.

Dry Reagent Assay

Formula:

For this formulation an aqueous dip at pH 6.25 can be applied separately from an ethanol dip, or two dips can be combined prior to impregnation and applied as one. The first dip dryer temperatures are 60/75/85° C., the second dip dryer temperatures are 40/50/60° C., and the one dip dryer temperatures are 40/50/60° C.

| Component | Concentration mM |
| --- | --- |
| Aqueous Dip: | |
| Buffer: N-(2-Acetamido)iminodiacetic Acid (ADA) | 300 |
| Ferric chloride | 5.1 |
| N(2-hydroxyethyl)ethylenediamine triacetic acid | 5.1 |
| Manganese II acetate | 13.2 |
| Sodium Dodecyl Sulfate (SDS) | 28 |
| Adjust pH to 6.25 with 10N NaOH | |
| Ethanol Dip: | |
| Tetramethylbenzidine (TMB) | 34.7 |
| Diisopropylbenzene dihydroperoxide (DBDH) | 65.0 |
| 4-Methylquinoline | 61.3 |
| 4-(4-Diethylaminophenylazo)benzene-sulfonic acid | |
| 4-(2-Hydroxy-(7,9-sodiumsulfonate)-1-naphthylazo)benzene | 0.55 |

Analysis:

Strips were made from papers produced from the dips listed above. Dose response curves of the K/S at 660 nm versus the concentration of hemoglobin in urine were generated by measurements with both the CLINI-TEK ® 10 and CLINITEK ® 200 Ames urine instruments. The slopes and intercepts of the dose response curves were determined and taken to represent reactivity and extent of blank reaction respectively.

Results:

Using the equation $$K/S = \sqrt{\frac{(1-R)^4}{4R^2}}$$

in which R is the reflectance from a test device, K is a constant and S is the light scattering coefficient of the particular reflecting medium (based on the Kubelka-Munk equation), the formulation with Mn II acetate had a 70% reduced K/S intercept. This reduction is the result of a considerably lower blank reaction than when MnII acetate is not in the formulation. The ascorbate resistance and dose response slopes are similar for papers with and without Mn II acetate. Paper made from the one dip process had a normal appearance after drying and was very responsive towards hemoglobin.

The present invention is defined by the claims which are provided below, and the present discussion is merely provided to help understand the claims and understand the numerous possible embodiments of the present invention as defined by the claims The limitations defining this invention are expressly outlined in the claims, and nothing provided in this discussion is intended to provide any additional limitations thereto.

What is claimed is:

1. An indicator composition which prevents metal-hydroperoxide or metal-peroxide mediated oxidation, said system comprising redox indicator buffer and at least 5 millimolar of a divalent metal complex of the general formula:

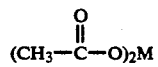

wherein M is either ZN(II), Co(II), Mn(II) or Rb(II).

2. The indicator composition of claim 1 wherein M is Zn(II).

3. The indicator composition of claim 1 wherein M is Co(II).

4. The indicator composition of claim 1 wherein M is Rb(II).

5. The indicator composition of claim 1 wherein M is Mn(II).